(12) United States Patent
Weilandt

(10) Patent No.: US 6,814,704 B2
(45) Date of Patent: Nov. 9, 2004

(54) DISPOSABLE NEEDLE GUIDE SYSTEM

(75) Inventor: Anders Weilandt, Sollentuna (SE)

(73) Assignee: Ascendia AB (SE)

( * ) Notice: Subject to any disclaimer, the term of this patent is extended or adjusted under 35 U.S.C. 154(b) by 50 days.

(21) Appl. No.: 10/239,551

(22) PCT Filed: Feb. 14, 2001

(86) PCT No.: PCT/SE01/00313

§ 371 (c)(1),
(2), (4) Date: Sep. 23, 2002

(87) PCT Pub. No.: WO01/62153

PCT Pub. Date: Aug. 30, 2001

(65) Prior Publication Data

US 2003/0171681 A1 Sep. 11, 2003

(30) Foreign Application Priority Data

Feb. 25, 2000 (SE) .............................................. 0000622

(51) Int. Cl.$^7$ ............................................... A61B 8/00
(52) U.S. Cl. ..................................................... 600/461
(58) Field of Search ................................. 600/461–471, 600/407, 409, 564–572, 437, 562, 576–579, 581

(56) References Cited

U.S. PATENT DOCUMENTS

| 4,898,178 | A | * | 2/1990 | Wedel ......................... 600/461 |
| 5,052,396 | A | | 10/1991 | Wedel et al. ........... 128/662.05 |
| 5,623,931 | A | * | 4/1997 | Wung et al. ................. 600/461 |
| 5,924,992 | A | * | 7/1999 | Park et al. ................... 600/461 |
| 5,992,899 | A | * | 11/1999 | Strowe .......................... 285/93 |
| 6,361,499 | B1 | * | 3/2002 | Bates et al. .................. 600/461 |
| 6,425,871 | B1 | * | 7/2002 | Jaggi ........................... 600/461 |

* cited by examiner

Primary Examiner—Francis J. Jaworski
(74) Attorney, Agent, or Firm—Ostrolenk, Faber, Gerb & Soffen, LLP

(57) ABSTRACT

A needle guide system for a medical imaging instrument comprises a needle guide assembly (1, 2) and a mounting assembly (3, 4, optionally 5) for attaching the needle guide assembly to a transducer, the mounting assembly comprising self-destroying means effective on dismounting. The mounting assembly comprises an attaching clip (4) mountable on a transducer directly or via an adapter (5), and a locking clip (3) mountable on the attaching clip from which it can be dismounted easily only by breaking indications of fracture comprised by the attaching clip. The needle guide assembly (1, 2) comprises a revolver (1) capable of receiving needles of varying diameter and a journal clip (2) by which it is mounted on the locking clip (3).

22 Claims, 6 Drawing Sheets

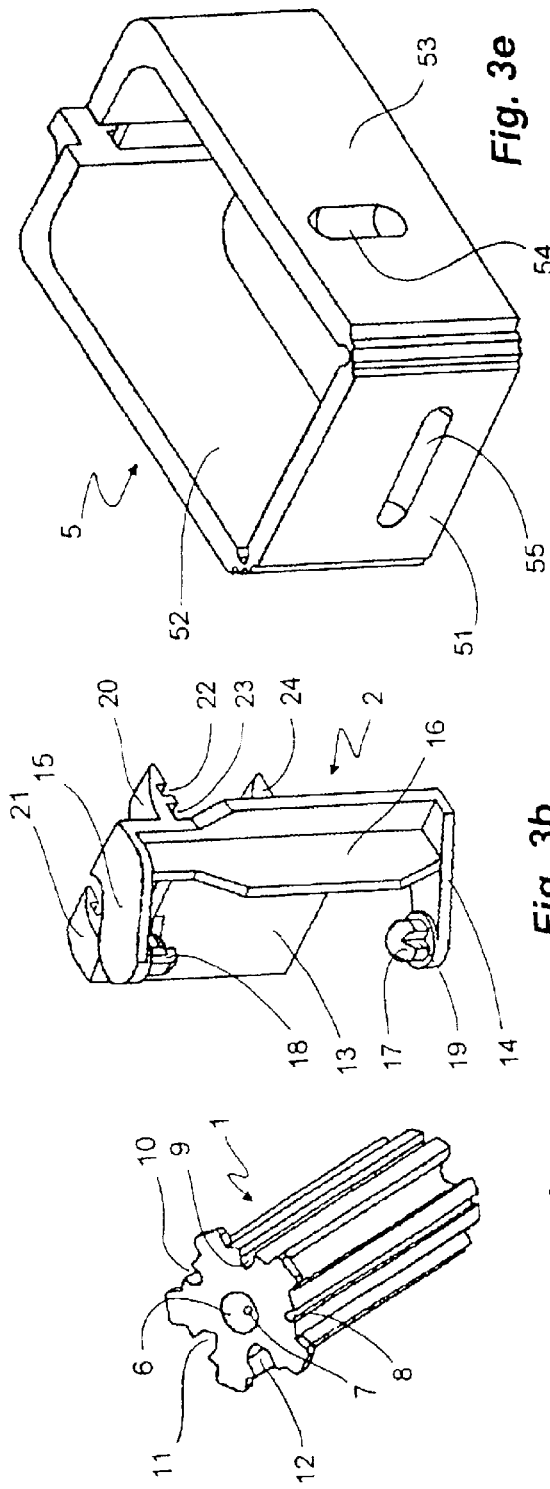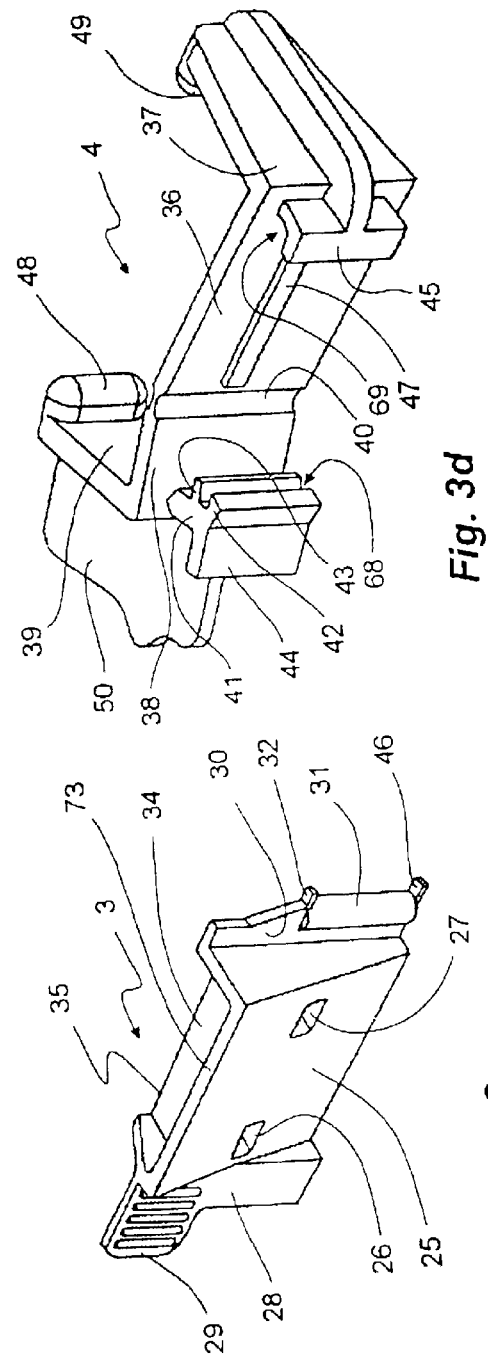

DISPOSABLE NEEDLE GUIDE SYSTEM

FIELD OF THE INVENTION

The present invention relates to a disposable needle guide system for a medical imaging instrument, in particular an ultrasonic transducer, for guiding a needle into a selected location of a patient relative to the imaging instrument, for use in percutaneous interventional procedures, such as fine needle aspiration, core biopsy, amniocentesis, and drainage.

BACKGROUND OF THE INVENTION

A great number of needle guide systems for use with ultrasonic transducers and the like are known in the art. Most of them are confined to be used with a transducer of particular geometry which is a considerable drawback in consideration of the considerable number of ultrasonic transducers of differing geometry on the market.

Another problem with most known needle guide systems is that they accept only one diameter size of needle, and that, therefore, their use with needles of different size necessitates the change of one or several parts. Present systems also suffer from the drawback that the user has to assemble the system from a number of parts. In addition most known needle guide systems require some sort of adapter which may constitute a substantial investment on its own. Also, such adapters may be lost or mislaid between individual percutaneous interventions.

A further problem with many known needle guide systems is that they are not truly disposable, that is, they are not easy and cheap to manufacture and, therefore, tend to be re-used, even if not suited or designed to be repeatedly used. They thus may constitute a risk to patients when being re-used improperly.

The present invention seeks to avoid the aforementioned problems.

OBJECTS OF THE INVENTION

It is an object of the present invention to provide a needle guide system of the aforementioned kind which can be adapted to transducers of varying shape, in particular ultrasound transducers.

It is another object of the present invention to provide a needle guide system of the aforementioned kind which has improved flexibility and functionality in comparison with needle guide systems presently in use.

It is an additional object of the invention to provide a needle guide system accepting needles of varying diameter without the need for exchanging parts.

It is a further object of the invention to provide a needle guide system which enables the user to choose between an adapter-based solution and a solution where a disposable device is directly fit to the transducer.

It is a particularly important object of the invention to provide a truly disposable needle guide system, that is, a system which cannot be re-used at all or with considerably difficulty only.

Further objects of the invention are evident from the following short description of the invention, the attached drawings illustrating a preferred embodiment, the detailed description thereof, and the appended claims.

SUMMARY OF THE INVENTION

According to the present invention is provided a needle guide system of the aforementioned kind, comprising a needle guide assembly and a mounting assembly for attaching the needle guide assembly to a transducer, the mounting assembly comprising self-destroying means effective on dismounting.

It is preferred for the needle guide assembly to comprise needle guide means accepting needles of different diameters, in particular needles from three to six different diameters.

It is also preferred for the needle guide means to comprise a revolver mounted in a stepwise lockable revolving manner on a journal clip.

The journal clip is mountable on the mounting assembly. According to the invention it is possible to provide a journal clip which can be mounted in two or more angular or height positions in respect of the mounting assembly.

According to a preferred aspect of the invention, the mounting assembly comprises an adapter mountable on a transducer, an attaching clip mountable on the adapter and a locking clip mountable on the attaching clip. It should be understood that the attaching clip is interposed between the adapter and the locking element on which the needle guide assembly is mountable.

It is however also possible for the attaching clip to be directly mountable the transducer; the portion of the transducer at which the attaching clip is mountable should be designed in a manner functionally corresponding to the mounting portion of the adapter. In such case no separate adapter will be needed. The variant of the needle guide assembly in which mounting portion of the adapter is comprised by the transducer is fully encompassed within the present invention.

It is preferred for the adapter to be of a generally abutable shape in respect of the transducer to which it is intended to be mounted in a transducer encircling position. The adapter preferably has two free ends provided with a cooperating snap connection which is closed on mounting and which is preferably not easily dismountable by hand.

According to a preferred second aspect of the invention the attaching clip comprises a base and first and second pairs of prehensile organs extending from the short or lateral ends of the base (or from positions close to the short ends) in opposite directions. A rough approximation of the general shape of a preferred attaching clip of the invention are two letters C joined back-to-back but not necessarily of the same size. The first pair of prehensile organs, such as claws, is designed in a manner to enable it to grip a U-formed portion of the adapter mounted on a transducer (or to directly grip a portion of the transducer of corresponding design) and to snap into position by its terminal portions interlocking with recesses provided in corresponding external faces of the adapter. Preferably further means for firmly attaching the adapter to the attaching clip are provided at facing faces of the attaching clip and the adapter, such as a transverse ridge disposed on an external face of the adapter insertable into a facing transverse recess disposed in the attaching clip.

According to a preferred aspect of the invention the claws of the second prehensile organ are adapted to grip opposite sides of the locking clip in a way so as to hold it against the attaching clip and locking it in this position. Once snapped into position the locking element is not easily removed by hand from the attaching clip.

The locking element preferably comprises a front and back support areas, such as support faces, grids or similar, tilting in respect to each other, the back face facing the attaching clip whereas the front face faces the needle is preferably selectable to fit a particular type of transducer or needle insertion depth.

The needle assembly is mountable on the mounting assembly by attaching the journal clip to the locking element. Preferably the journal clip is mounted in a manner making it difficult or impossible to remove it from the locking element in a mounted position, for instance by snap tongues inserted into through openings in the locking element into which they lock and/or by snap tongues which can grip edges of the locking element.

It is preferred for the needle guide system of the invention to be easily detachable from a position mounted on a transducer only by damaging (breaking) a weak point, such as a fracture zone or line, of the mounting assembly. Particularly preferred is for such a weak point, kerf or facture zone to be comprised by the second prehensile means, in particular by one claw thereof.

It is preferred for the attaching clip to comprise breaking means for such destructive dismounting, the breaking means comprising a twisting element and a fracture zone or line. It is preferred for the fracture zone or line to be easily broken by displacement of sections adjacent to the zone or line in the direction of the transducer axis. Particularly preferred is the removal of a support for one or both second prehensile means providing for release of the locking element. By making the dismounting of the attaching clip conditional on its destruction the unsafe re-use of the needle assembly is prevented.

It is preferred for the revolver to comprise a multitude of needle receiving slots, for instance, three to six slots, each slot being dimensioned to receive a needle of different diameter. The revolver has about cylindrical shape with the slots disposed in its mantle in parallel with the cylinder axis and in an about equidistant manner along its circumference corresponding to an exactly equidistant manner in regard of the axes of their respective needles. Whereas the width of each slot corresponds closely to the diameter of the needle which it is intended to receive, its depth is slightly less than said diameter. Thereby the needle protrudes somewhat in a radial direction from the slot.

It is furthermore preferred for the revolver to comprise a multitude of locking elements. The locking elements, for instance, radially extending locking ribs, are arranged for locking the revolver in a position in which the a needle disposed in the slot of corresponding diameter is made abut a recess in a wall of the angular clip facing away from the transducer. Thereby the displacement of the needle is restricted to be strictly axial.

According to the present invention is also provided a disposable needle guide system comprising a needle guide assembly and a mounting assembly mountable on a transducer, the mounting assembly comprising an attaching clip mountable on a mounting portion of the transducer or on an adapter mountable on the transducer, and a locking clip mountable on the attaching clip so as to be releaseably held at its opposite ends by holding portions of the attaching clip, the release means including a kerf or other indication of fracture comprised by a support portion of the attaching clip supporting one of said holding portions and being easily breakable by hand. It is preferred for the release function to comprise a handle which can be turned to break the kerf or other indication of fracture and thereby irreversibly release the locking clip.

If not indicated otherwise, in this specification the orientation of the various elements of the needle guide system of the invention is in relation to the transducer. Ultrasound and other transducers are normally of a cylindrical, rectangular, parallelepipedeal or similar configuration for which a longitudinal axis can be defined. Directions perpendicular to that axis are termed "transverse" or "lateral". Faces facing the transducer are termed "interior" or "inwardly facing" or similar. Faces facing away from the transducer are termed "exterior" or "outwardly facing" or similar.

BRIEF DESCRIPTION OF THE DRAWINGS

In the following the invention will be explained in greater detail by reference to preferred embodiments illustrated in a raw drawing showing in FIG. 1 a first embodiment of the needle guide system according to the invention mounted on an ultrasonic transducer, in a perspective view and with the transducer not shown;

FIGS. 3a–e, the individual elements of the embodiment of FIG. 1, in substantially the same view as in FIG. 1;

DETAILED DESCRIPTION OF PREFERRED EMBODIMENTS

Figure 1:
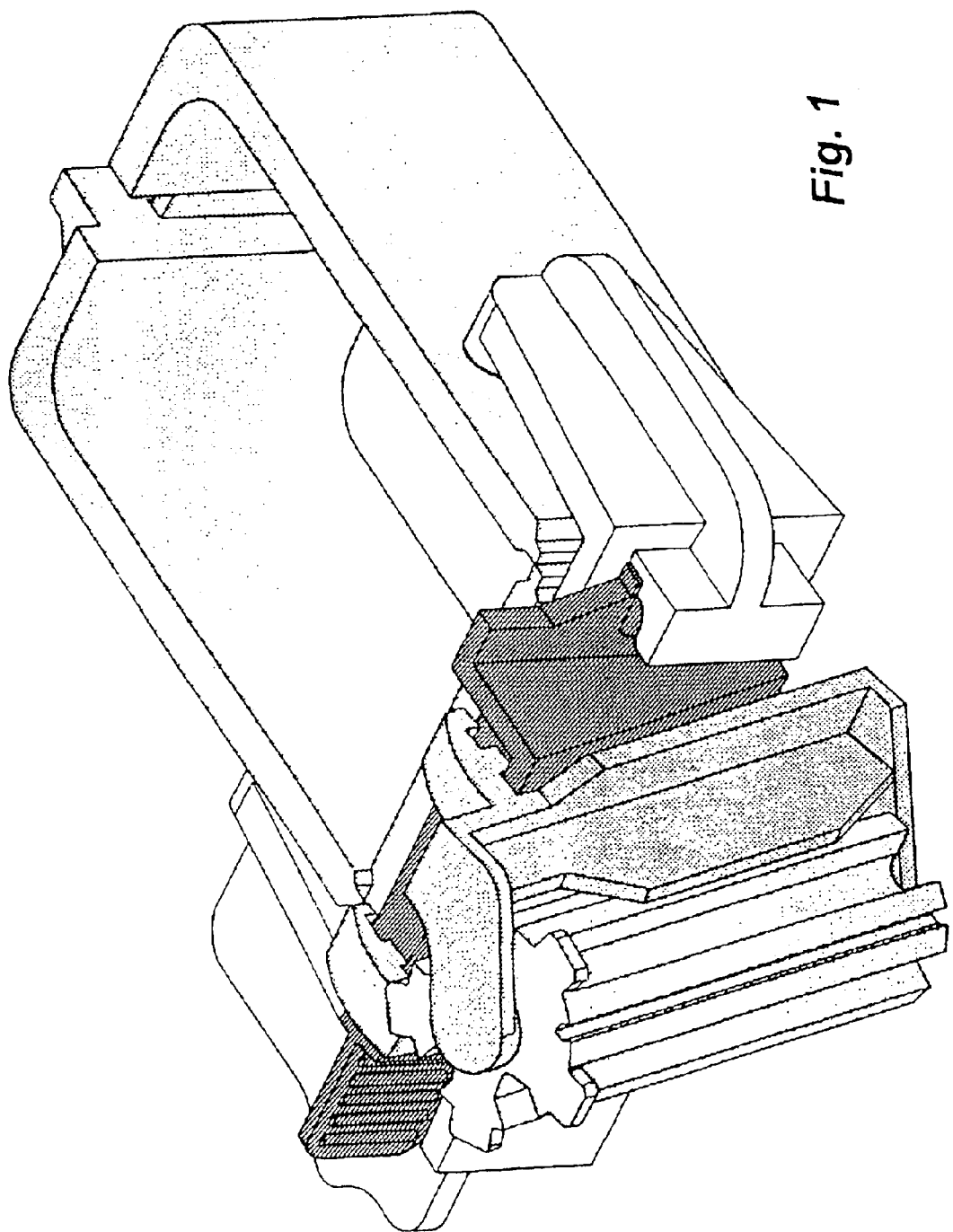

The first embodiment of the needle guide system of the invention shown in FIGS. 1–5 comprises five elements: a revolver 1, an journal clip 2, a locking clip 3, an attaching clip 4, and an adapter 5. The elements 1–5 are preferably made of suitable polymer material(s).

The revolver 1 is mounted rotatably between lower 14 and upper 15 arms of the journal clip 2 extending from a base plate 13 and carrying bearing necks 17 and 18, respectively, which extend into a central bore 6 of the revolver at its respective ends. Juts 7 are disposed in the bore 6 close to its lower and upper end for snapping interaction with catches 19 on the bearing necks 17,18. Five such catches 19 are symmetrically arranged on each bearing neck 17;18 allowing the revolver 1 to be displaced between five fixed positions by hand. These fixed positions correspond to five axial slots 8–12 on the revolver 1, each slot being dimensioned to receive a hypodermic needle 70 of certain width. Thereby the needle guide of the invention can be used with needles of various (standard) dimensions. For mounting the needle 70 is placed in the slot 10 of corresponding width, and the revolver 1 with the needle 70 in the slot 10 is rotated until the needle 70 is locked in the slot 10 by the abutting the base plate 13 at a shallow indentation (not shown). The locking mechanism uses the resilient nature of the polymer materials of the revolver 1 and the journal clip 2; it does not prevent the needle from being moved in the direction of the slot 10. The journal clip 2 comprises a stiffening rib 16. It is useful to provide the journal clip 2 and the elements 3 and 4 with further stabilizing structures like the stiffening rib 16 but is not shown in the drawing for the sake of clarity. How the journal clip 2 with the revolver 1 is mounted on the remainder of the needle guide system by of upper 20,21 and lower 24 claws extending from the rear side of the base plate 13 (the side facing away from the revolver 1) will be explained later.

The needle guide assembly of the invention can be mounted on transducers of different geometry by an adapter 5 designed to fit the individual transducer. It is also possible to incorporate the portion of the adapter at which the remainder of the needle guide assembly is to be mounted in the transducer; in such case a separate adapter becomes superfluous. Only one external wall (a wall facing away from the transducer) of the adapter 5 (or the transducer, if no separate adapter is being used) need to be designed in a standard manner so as receive the remaining needle guide system elements 1–4.

This wall is the facing wall of the base plate 51 in FIG. 3e. The base plate 51 forms part of a belt structure comprising left 52 and right 53 arms provided with angular end portions 64,63 and joined to the base plate 51 by right 56 and left 57 thin flexible hinge sections. On mounting the base plate 51 on a transducer 71 its internal wall is pressed against the corresponding transducer wall, the arms 52, 53 are folded towards each other so as to enclose the transducer 71, and the adapter 5 is secured at the transducer 71 by a snap connection 65,66,67 disposed at the external walls of it angular end portions 63,64 comprising a tongue 65 with a head 66 integral with the right end portion 63 insertable into a catch 67 integral with the left end portion 64. The snap connection 65,66,67 is of a self-locking sort that is not easily disassembled by hand.

The journal clip 2 with the revolver 1 is attached to and locked on the adapter 5 by means of an attaching clip and a locking clip.

The attaching clip 4 comprises a base plate separated into right 36 and left 38 sections by a thin-walled flexible bridge 40 which has a hinge function. To the right section 36 is joined a claw 37 at a right angle provided with an inwardly extending claw head 49. To the left section 38 is joined a left claw 39 at a right angle provided with an inwardly extending claw head 48.

Figure 2:
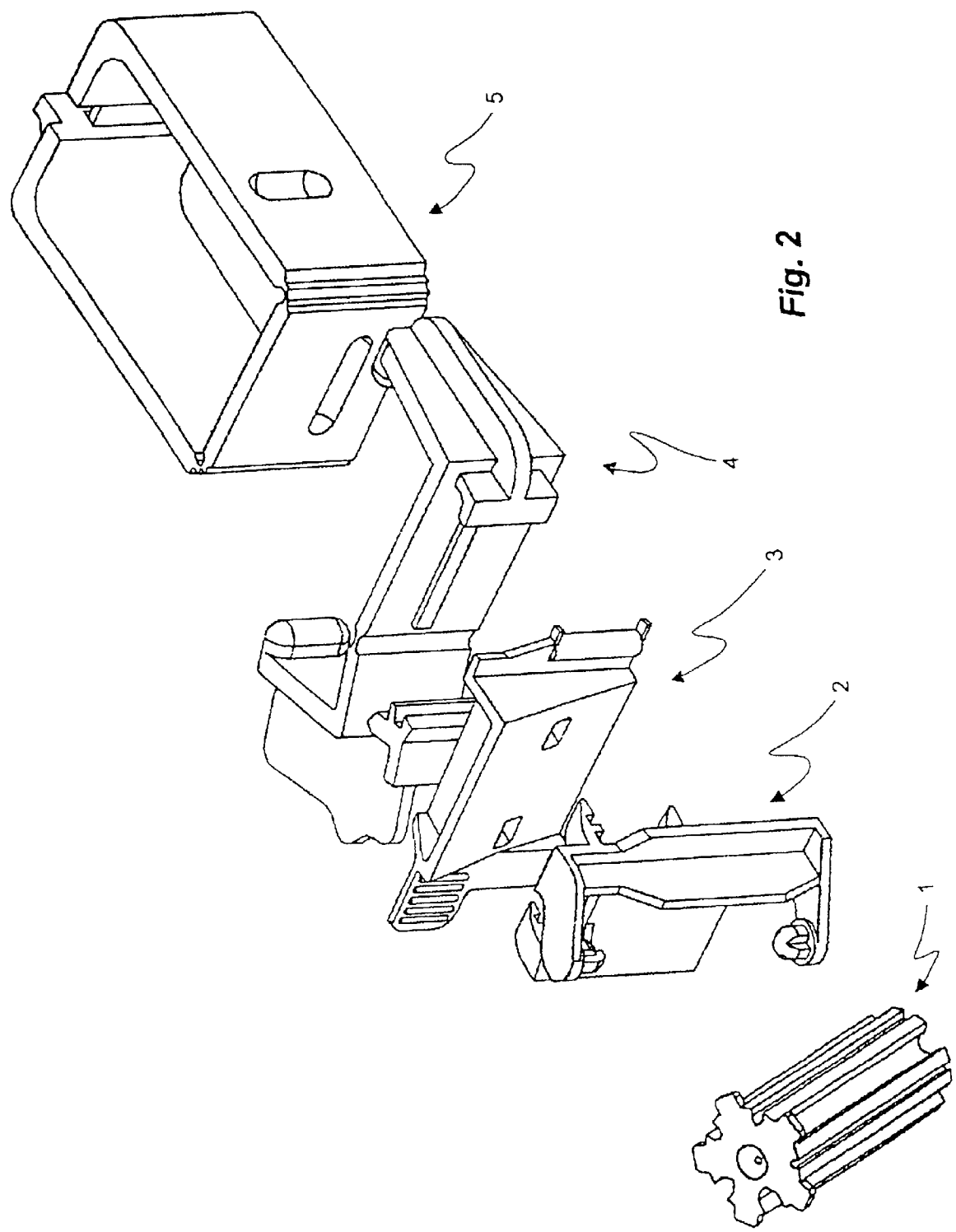
FIG. 2 the embodiment of FIG. 1, in an exploded view.
Figure 4:
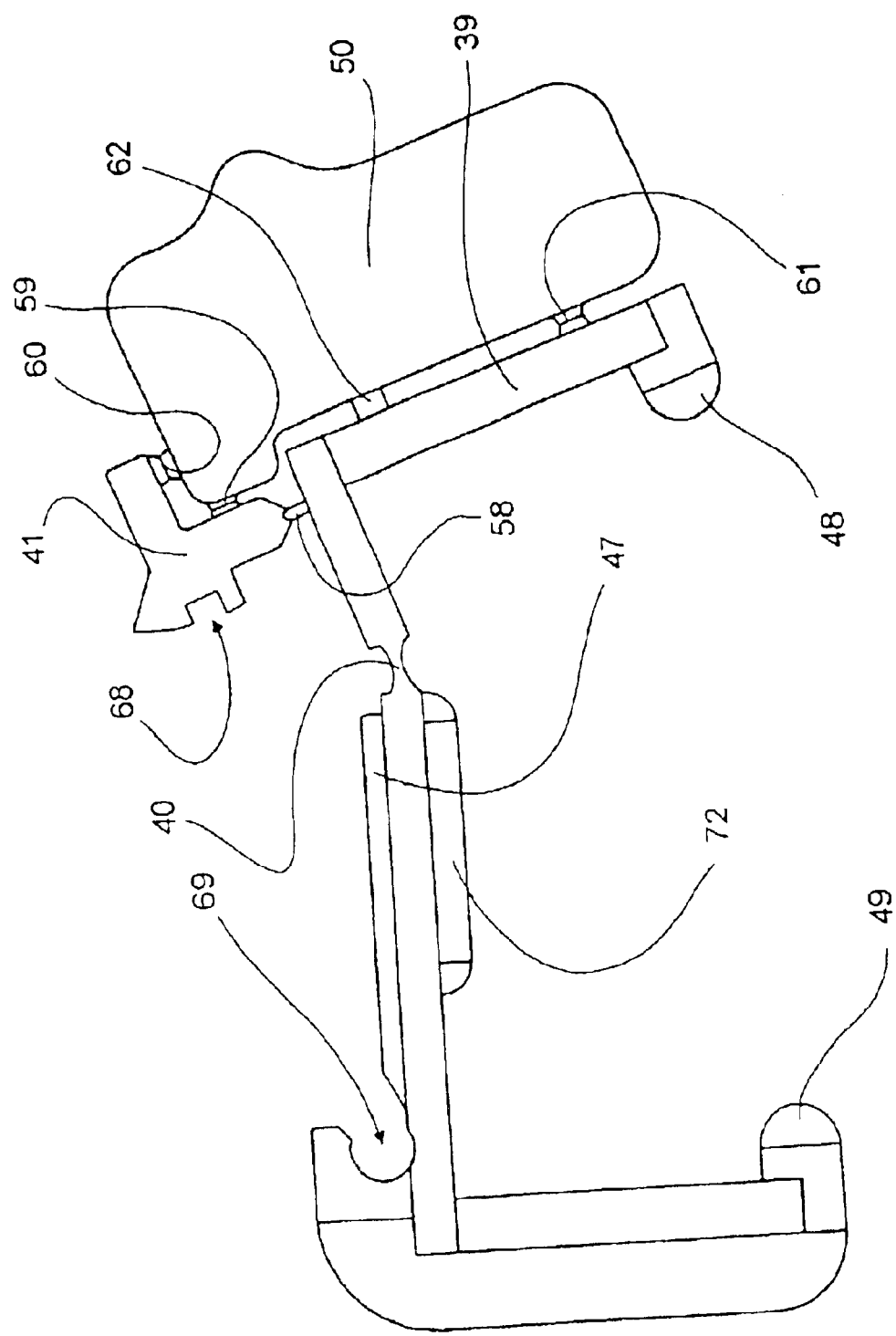
FIG. 4 the adapter of the embodiment of FIG. 1 in an unmounted state, in a bottom view.
Figure 5:
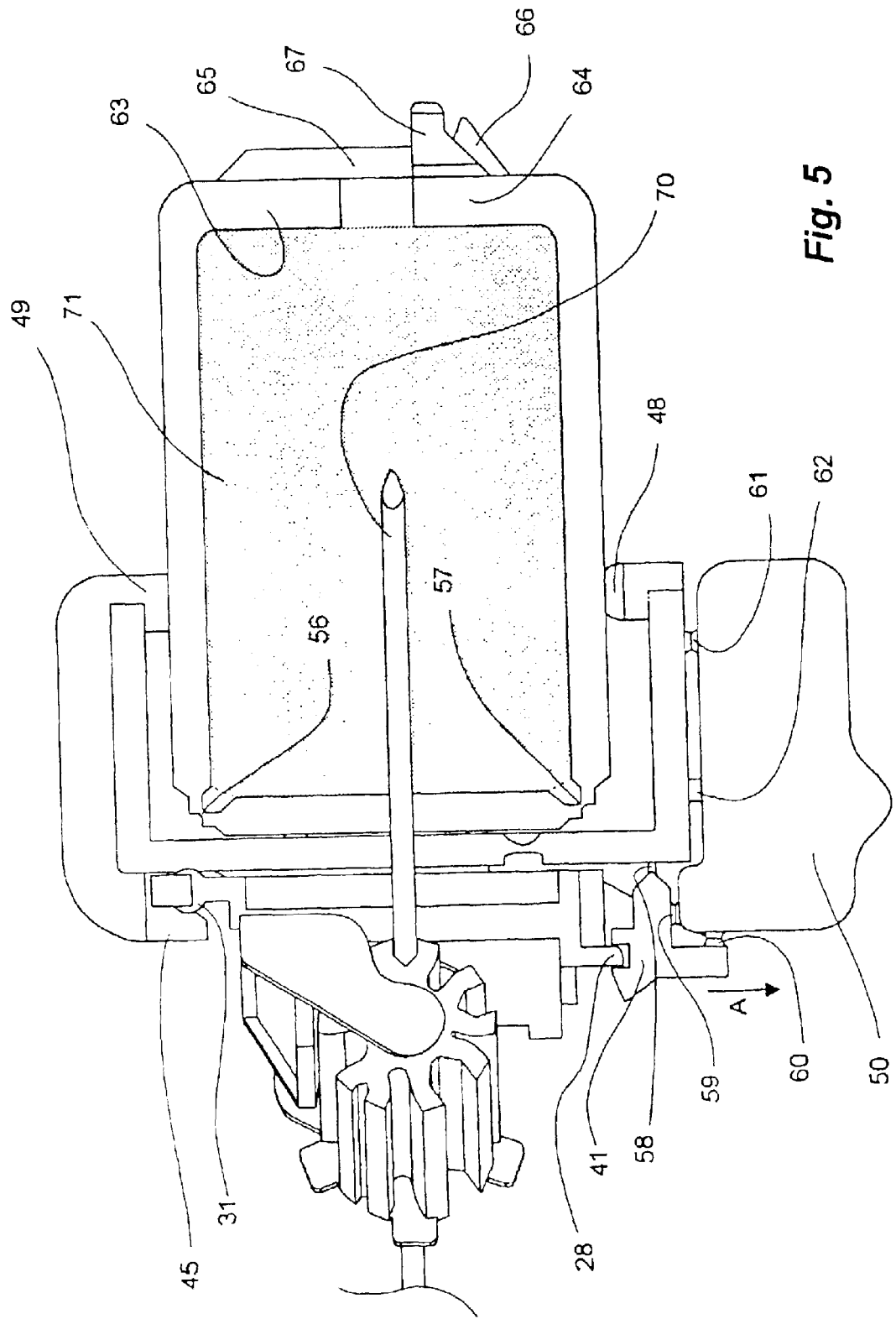
FIG. 5 the embodiment of FIG. 1 with the transducer shown and a hypodermic needle mounted, in a bottom view.

The attaching clip 4 is placed with its left right base plate section 38 against the external face of the adapter base plate 51 so as to make a retainer key 72 disposed at the interior face of left section 36 fit into a recess 55 disposed on the exterior face of the adapter base plate and the right claw head 49 fit into a recess 54 disposed at the external face of the right arm 53 of the adapter 5. Then the left section 38 is swiveled around the flexible bridge 40 which forms a sort of hinge until it abuts the adapter base plate 51; thereby the right claw head 48 is inserted in recess (not shown) disposed on the external face of the adapter left arm 52 corresponding to recess 54. In FIGS. 2–4 the attaching clip 4 is shown in a state prior to it being clamped on adapter 5.

The attaching clip 4 is locked on the adapter 5 by means of the locking clip 3 which comprises two faces, an outwardly facing first face identical with the exterior face of a base plate 25 and an inwardly facing second face defined by the internal face of a right locking flange 30 provided with a locking cylinder 31 and the internal face of a transverse stiffening rib 34 as well as the internal faces of vertical stiffening ribs (not shown) extending downwards from rib 34. The first face is tilted in respect of the second face by an angle of about 15°. The internal face of the locking clip comprises a recess (not shown) which is engageable with a retainer key 47 disposed at the external face of the right base element section 36.

For locking the locking 3 on the attaching clip 4 the former is provided with laterally extending left 28 and right 30 locking arms, the right locking arm comprising a cylindrical end portion 31 from which upper 32 and lower 46 projections extend and the left locking arm comprising a handle 29. The left and right locking arms 28,30 are insertable into the gaps 68,69 of left 41 and right 45 locking clip holders arranged on the external faces of the left 38 and right 36 attaching clip base plate sections. The left locking clip holder comprises clamping flanges 42,43 and a rear support portion 44. In combination with the cylindrical end portion 31 of the right locking arm 30 the right locking clip holder 45 provides a slight hinge function used on mounting: the cylinder portion 31 of locking clip 3 is first inserted into gap 69 of the right locking clip holder 45; then the left side of locking clip 3 is flipped towards clamp flange 42 of the left locking clip holder 41 to make it snap into its gap 68 from which position it is not easily dismounted by hand. The locking clip 3 furthermore is locked in this position by a retainer key 47 disposed on the external face of the right section 36 of the attaching clip base plate engaging with a grove and rib indentations (not shown) disposed on the internal face of the locking clip 3.

The journal clip 2 with the revolver 1 is mounted on the locking clip by inserting a pair of lower claws 24 (only one shown) disposed on the interior face of base plate 13 of the journal clip 2 into claw ducts 26,27 penetrating the locking clip base plate 25, the claws being retained in the ducts 26,27 by keyways (not shown) engaging with the base plate. Simultaneously a pair of upper claws 20, 21 disposed on the interior face of base plate 13 of the journal clip 2 above said lower claws 24 are pushed over the top face 73 of the locking clip base plate 25 with which they engage by keyways 22, 23 in two selectable positions providing for different angles of hypodermic needle orientation. Thereby the journal clip 2 is locked on the locking clip 3 in a irreversible manner since the snap connection provided by claws 20,21,24 is not easily dismounted by hand.

The various snap connections make use of the resiliency of selected polymer materials.

As already pointed out the various snap connections in combination with the design of the needle guide system according to the invention provide for the mounted system not being easily dismountable in its integrity, thus preventing unauthorized multiple use which might put the patient at risk.

The needle guide system according to the invention can be easily dismounted only by damaging an important component, the attaching clip. To this effect, the attaching clip is provided with an arrangement supporting the left locking clip holder 41 which is attached to the left base plate section 38 by a rather thin bridge 58 of material which is sufficiently stable to provide support (in a mounted position) in direction perpendicular to the base plate and parallel with grove (gap) 68 but not in a transverse direction indicated by arrow A in FIG. 5. In that transverse direction the clip holder 41 is supported by a release grip 50 via supports 59 and, to a lesser degree, 60. The clip holder 50 is attached to the external face of the left claw 39 by a hinge pin 62 and a further support 61. The supports 59,60,61 are designed to be easily broken by relative displacement of the elements which they connect in a perpendicular direction. This capability is used when releasing the left locking clip holder 41 by turning the release grip around the hinge pin 62. The hinge pin 62 is not and need not be a pin freely rotatable in a bearing or hinge, it is sufficient that the material constituting it allows the clip holder 50 to be rotated by hand while being sufficiently rigid to hold the clip holder 50 in position against the pressure exerted by the mounted locking clip 3 in normal use. The breaking of supports 59,60 on rotating clip holder 50 out of its plane allows the left locking clip holder 41 to flip away from the locking clip 3 in the direction of arrow A, thus allowing the locking clip 3 with the journal clip 2 and the revolver 1 to be removed. Thereby the attaching clip 4 can be folded away from the adapter 5 (in the direction of arrow B) and removed. The pressure exerted on the adapter 5 by claws 37,39 thus comes to an end which facilitates its dismounting.

Figure 6:
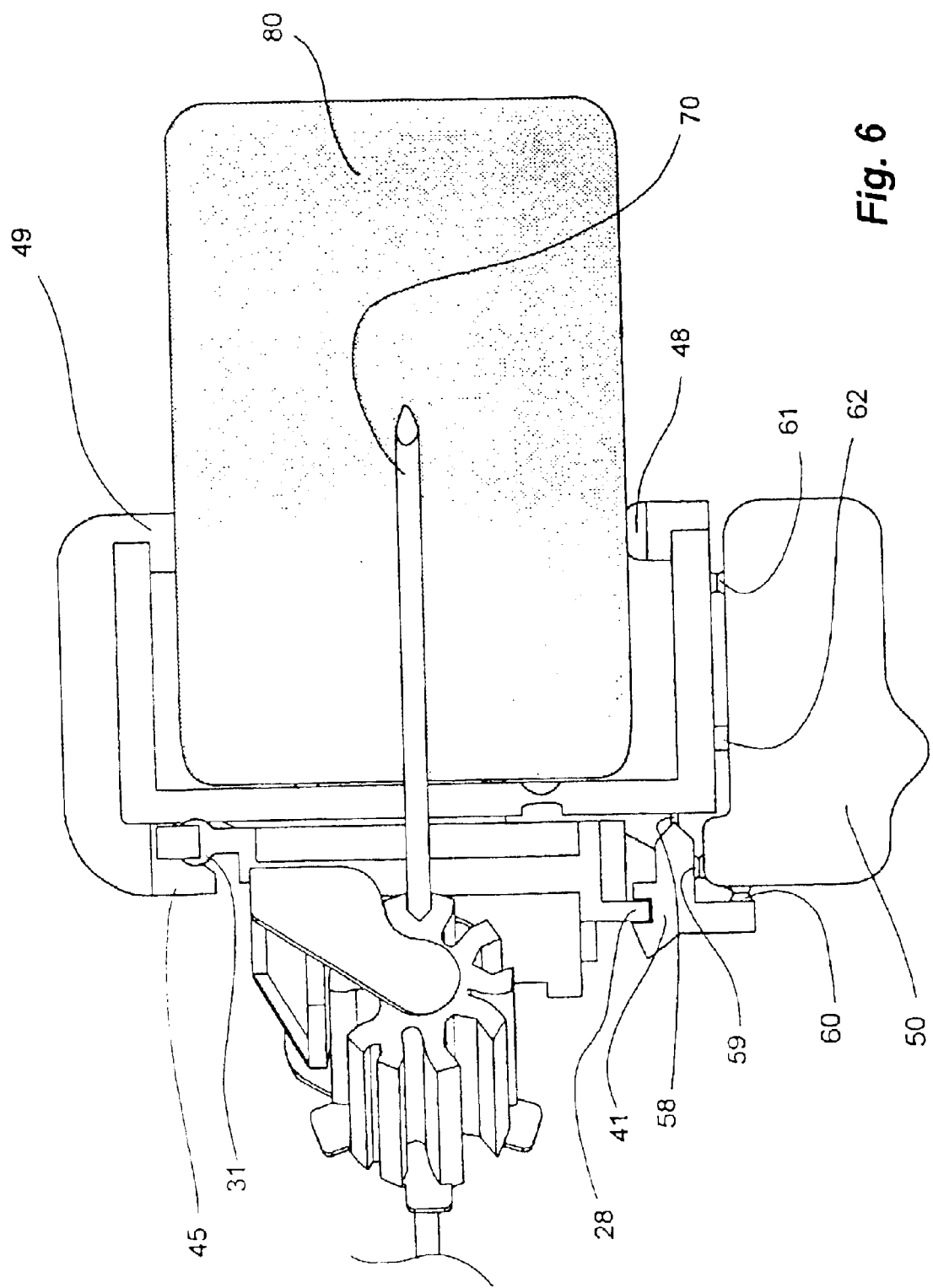
FIG. 6 a second embodiment of the needle guide system according to the invention, in the same view as in FIG. 5.

The second embodiment of the needle guide system of the invention shown in FIG. 6 comprises four elements: a revolver 1, an journal clip 2, a locking clip 3, and an attaching clip 4. The four elements 1,2,3,4 of the second embodiment fully correspond to elements 1,2,3,4 of the first embodiment and are therefore identified by same reference numbers. In the second embodiment the mounting portion of the adapter 5 of the first embodiment is incorporated in the transducer 80 on which the attaching clip 4 is directly mounted.

What is claimed is:

1. A needle guide system for a medical imaging instrument, for guiding a needle into a selected location of a patient relative to the imaging instrument, for use in percutaneous interventional procedures, comprising a needle guide assembly and a mounting assembly for attaching the needle guide assembly to a transducer, the mounting assembly comprising a self-destroying element configured to be effective on dismounting from the transducer so that the needle guide assembly is prohibited from reuse.

2. The needle guide system of claim 1, comprising needle guide means accepting needles of different diameter.

3. The needle guide system of claim 2, wherein the needle guide means comprise a revolver mounted in a stepwise lockable revolving manner on a journal clip.

4. The needle guide system of claim 3, wherein the journal clip is mountable on the mounting assembly.

5. The needle guide system of claim 4, where the journal clip is mountable in two or more angular or height positions in respect of the mounting assembly.

6. The needle guide system of claim 1, wherein the mounting assembly comprises an adapter mountable on a transducer, an attaching clip mountable on the adapter and a locking clip mountable on the attaching clip.

7. The needle guide system of claim 6, wherein the adapter is of a generally abutable shape in respect of the transducer to which it is intended to be mounted in a transducer encircling position.

8. The needle guide of claim 6, wherein the adapter has two free ends provided with a cooperating snap connection which is closed on mounting and which is not easily dismountable by hand.

9. The needle guide system of claim 6, wherein the attaching clip comprises a base and first and second prehensile organs such as pairs of claws extending in opposite directions from the short or lateral ends of the base or from positions close to the short ends.

10. The needle guide system of claim 9, wherein the first prehensile organ is designed for gripping a U-formed portion of the adapter mounted on a transducer.

11. The needle guide system of claim 9, wherein the second prehensile organ is designed for gripping opposite sides of the locking clip so as to hold the locking clip against the attaching clip and locking it in this position.

12. The needle guide system of claim 1, wherein the mounting assembly comprises an attaching clip mountable on the transducer and a locking clip mountable on the attaching clip.

13. The needle guide system of claim 12, wherein the attaching clip comprises a base and first and second prehensile organs such as pairs of claws extending in opposite directions from the short or lateral ends of the base or from positions close to the short ends.

14. The needle guide system of claim 13, wherein the first prehensile organ is designed for gripping a portion of the transducer.

15. The needle guide system of claim 13, wherein the second prehensile organ is designed for gripping opposite sides of the locking clip so as to hold the locking clip against the attaching clip and locking it in this position.

16. The needle guide system of claim 12, wherein the needle guide assembly is mountable on the mounting assembly by attaching the journal clip to the locking element.

17. The needle guide system of claim 16, wherein the journal clip is mounted in a manner making it difficult or impossible to remove it from the locking element.

18. The needle guide system of claim 6, wherein the needle guide assembly is mountable on the mounting assembly by attaching the journal clip to the locking element.

19. The needle guide system of claim 18, wherein the journal clip is mounted in a manner making it difficult or impossible to remove it from the locking element.

20. The needle guide system of claim 1, designed to be detachable from a position mounted on a transducer only by breaking a kerf or a fracture zone or line of the mounting assembly.

21. The needle guide system of claim 20, wherein the kerf or facture zone or line is comprised by the second prehensile means.

22. A disposable needle guide system comprising a needle guide assembly and a mounting assembly mountable on a transducer, the mounting assembly comprising an attaching clip mountable on a mounting portion of the transducer or on an adapter mountable on the transducer, and a locking clip mountable on the attaching clip so as to be releasably held at its opposite ends by holding portions of the attaching clip, the release means including a kerf or other indication of fracture comprised by a support portion of the attaching clip supporting one of said holding portions and being easily breakable by hand.

* * * * *